United States Patent
Ramtoola

(10) Patent No.: US 9,271,942 B2
(45) Date of Patent: Mar. 1, 2016

(54) METHOD OF PRODUCING MICROCAPSULES

(75) Inventor: Zebunnissa Ramtoola, Dublin (IE)

(73) Assignee: ROYAL COLLEGE OF SURGEONS IN IRELAND, Dublin (IE)

( * ) Notice: Subject to any disclaimer, the term of this patent is extended or adjusted under 35 U.S.C. 154(b) by 1033 days.

(21) Appl. No.: 12/513,390

(22) PCT Filed: Nov. 7, 2007

(86) PCT No.: PCT/IE2007/000108
§ 371 (c)(1),
(2), (4) Date: May 17, 2011

(87) PCT Pub. No.: WO2008/056344
PCT Pub. Date: May 15, 2008

(65) Prior Publication Data
US 2011/0212180 A1 Sep. 1, 2011

(30) Foreign Application Priority Data
Nov. 7, 2006 (EP) ..................................... 06394021

(51) Int. Cl.
*A61K 9/50* (2006.01)

(52) U.S. Cl.
CPC .............. *A61K 9/5026* (2013.01); *A61K 9/5031* (2013.01); *A61K 9/5036* (2013.01); *A61K 9/5047* (2013.01)

(58) Field of Classification Search
None
See application file for complete search history.

(56) References Cited

U.S. PATENT DOCUMENTS

| 6,238,690 | B1 * | 5/2001 | Kiefer et al. | 424/439 |
| 2002/0050659 | A1 * | 5/2002 | Toreki | A01N 25/006 264/4.1 |
| 2002/0054912 | A1 | 5/2002 | Kim et al. | |
| 2006/0068019 | A1 * | 3/2006 | Dalziel et al. | 424/490 |
| 2007/0141211 | A1 * | 6/2007 | Kolar, Jr. | A23D 9/06 426/302 |

FOREIGN PATENT DOCUMENTS

| EP | 0 423 701 | 4/1991 |
| EP | 0 525 731 | 2/1993 |
| EP | 0 573 978 | 12/1993 |
| EP | 1 240 883 | 5/2002 |

OTHER PUBLICATIONS

"Xylitol—Wikipedia" [retrieved on Oct. 1, 2014]. Retrieved from the Internet: http://en.-wikipedia.org/wiki/Xylitol.*

* cited by examiner

*Primary Examiner* — David J Blanchard
*Assistant Examiner* — Daniel F Coughlin
(74) *Attorney, Agent, or Firm* — Nixon Peabody LLP

(57) ABSTRACT

A method of producing microcapsules of the type having a core and a coating encapsulating the core comprises the steps of providing a core-forming fluid stream and a coating-forming fluid stream, providing a two spray nozzle arrangement having a core nozzle disposed concentrically about a second nozzle, spraying the core-forming fluid stream from the core nozzle and the coat-forming fluid stream from the concentric nozzle to produce microcapsules, and solidifying the microcapsules upon formation in a suitable gas. Spray drying or spray chilling may be employed as the means of solidifying the microcapsules. Microcapsules having a core and a solid coat are also described.

6 Claims, 3 Drawing Sheets

Figure 1 (Comparative)
One liquid stream- liquid A
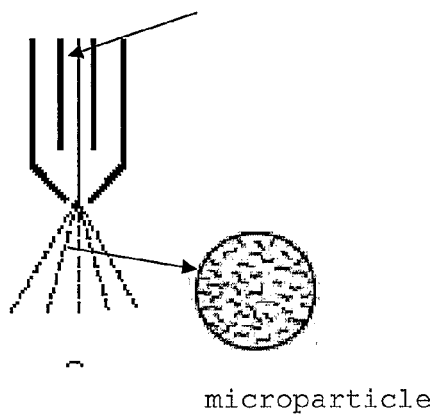
microparticle
Figure 2
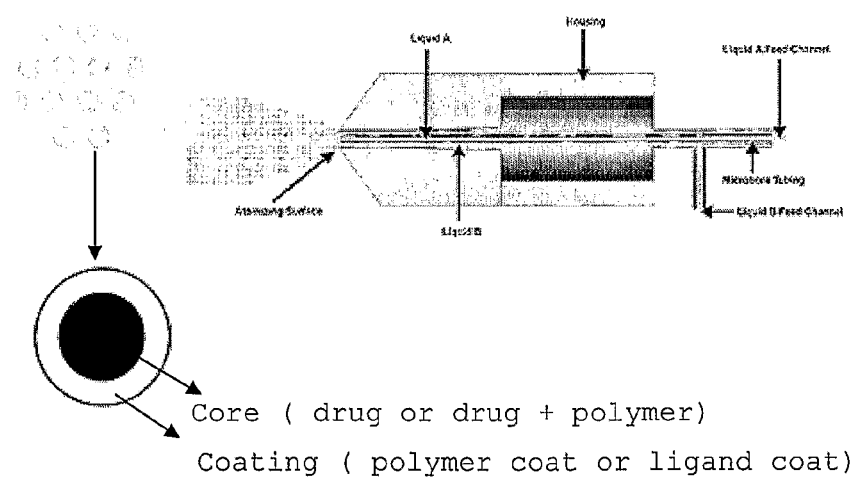
Core ( drug or drug + polymer)
Coating ( polymer coat or ligand coat)

Figure 3
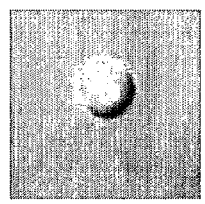
Sample 1
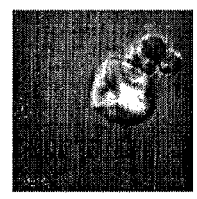
Sample 2
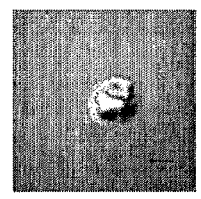
Sample 4
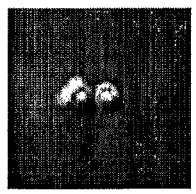
Sample 1
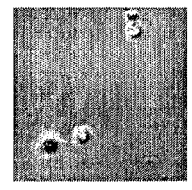
Sample 3
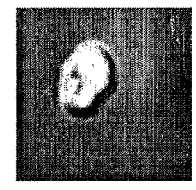
Sample 4

Figure 4
sample 5
sample 6
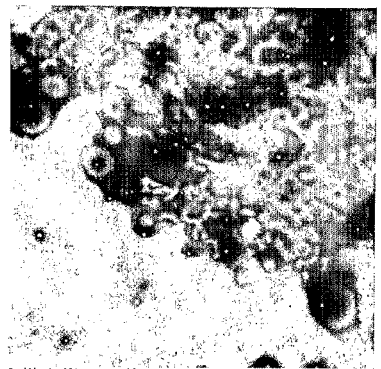
sample 7
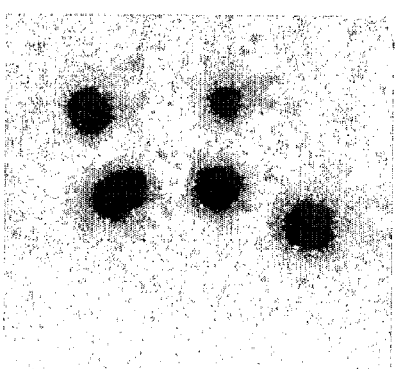
sample 8

METHOD OF PRODUCING MICROCAPSULES

CROSS-REFERENCE TO RELATED APPLICATIONS

This application is the National Stage of International Application No. PCT/IE2007/000108 filed Nov. 7, 2007, which claims the benefit of European Application No. 06394021.7, filed on Nov. 7, 2006. The contents of both applications are hereby incorporated by reference in their entirety.

TECHNICAL FIELD

The invention relates to a method of producing microcapsules having a core and a coating encapsulating the core. The invention also relates to microcapsules formed according to the methods of the invention.

BACKGROUND TO THE INVENTION

Microencapsulation is a widely utilised process in the pharmaceutical industry for applications in delayed release, sustained release and targeting of administered drugs to their optimum site of absorption and/or action. In addition microencapsulation can be used to mask unpleasant taste and to protect drug from environmental influences such as oxidation or from contact with other incompatible material/actives. A range of techniques exist for microencapsulation, including coacervation, solvent evaporation from emulsions, and fluid bed coating.

Spray drying is among the most efficient and widely used technique for the drying of liquids and slurries. It is reliable, reproducible and is a one-step continuous procedure offering easy scale-up. Spray drying is a technique where a liquid stream is sprayed through a nozzle into a chamber with hot circulating gas such as air, nitrogen or argon. Droplets formed at the nozzle are dried in the hot gas resulting in the formation of particles. The resulting dried material usually is microparticles consisting of a uniform mix of the various components of the spray dried solution as shown in FIG. 1.

STATEMENTS OF INVENTION

According to the invention, there is provided a method of producing microcapsules of the type having a core and a coating encapsulating the core, the method comprising the steps of providing a core-forming fluid stream and a coating-forming fluid stream, providing a two spray nozzle arrangement having a core nozzle disposed concentrically about a second nozzle, spraying the core-forming fluid stream from the core nozzle and the coat-forming fluid stream from the concentric nozzle to produce microcapsules, and solidifying the microcapsules upon formation in a suitable gas.

Thus, the method essentially comprises the steps of spraying a fluid stream through a nozzle to produce droplets, and drying (as in a spray drying process) or hardening (as in a spray chilling process) the droplets in air. Generally, the air will be hot air which dries the microcapsules as they leave the nozzle. However, in the case of spray chilling, in which case the fluid stream(s) comprise lipids and/or waxes and/or low melting point polymers, which are heated to melt these components, the microcapsules formed at the nozzle are solidified in cold air as opposed to hot air. General details of spray chilling methodology are available in the Quick Operation Guide provided with the Spray Chilling Accessory from Buchi.

Generally, the method is characterised over conventional spray drying or spray chilling insofar as the nozzle comprises a core nozzle through which a core-forming fluid is sprayed and a second nozzle formed concentrically about the core nozzle and through which a coat-forming fluid stream is sprayed. The droplets formed by the double nozzle arrangement comprise a core of the first fluid and a coating of the second fluid. In a preferred embodiment of the invention, the coating wholly encapsulates the core.

In the case of spray drying, the hot gas is typically air or a different gas like an inert gas such as nitrogen, argon or other inert gases. In the case of spray chilling, air at ambient temperature of 45° C. or below is generally used.

Typically, the core-forming fluid is a liquid or a gas. When it is of a liquid nature, it is selected from the group comprising: a solution; a suspension; a dispersion; a colloidal solution or dispersion; an oil; and an emulsion. Suitably, the core-forming liquid comprises an active compound or substance, optionally in combination with one or more pharmaceutically acceptable excipients. The active compound or substance may be any type of therapeutic, prophylactic, diagnostic, or prognostic agent. Further, it may be an agent used in imaging or labelling. In one preferred embodiment, the agent may be a pharmaceutically active agent that is required to be released in a controlled manner; thus, the coating may be designed to break down slowly in a physiological environment to release the encapsulated core over a period of time.

Typically, the core comprises a material/substance that is different to the material/substance of the coating.

Optionally the core may include a sustained release polymer with the coat being a second controlled release polymer with/without one or more targeting moieties.

In one embodiment, the core-forming fluid may comprise or consist of a gas or a volatile solvent such as but not limited to ethanol, acetone, or ethylacetate. The gas may be selected from the group comprising: air; an inert gas; a gas suitable for imaging applications; or mixtures thereof. The use of a gaseous core finds particular application in microcapsules for pulmonary delivery, the gaseous core providing a microcapsule of low density more suited for delivery as an aerosol.

In one embodiment of the invention, the coat-forming fluid comprises a coating material capable of forming a film or wall around the core material. Ideally, the coating material is capable of forming a film or wall that wholly encapsulates the core material. In this specification, the term "wholly encapsulates" should be understood as meaning a coating that wholly or predominantly covers the core. Suitably, the coat forming fluid comprises a component selected from the group comprising: polymer; lipid; wax; surfactants; surface stabilising agents; and a ligand suitable for targeting the microcapsules to a specific desired site of action in the body. Suitably, the polymer is selected from the group comprising: methacrylate polymers such as Eudragit polymers; ethylcellulose polymers; biodegradable polyesters such as poly-lactide (PLA), poly-glycolide (PGA), and copolymers of lactic and glycolic acid, poly-lactide-co-glycolide (PLGA, poly-caprolactone (PCA); poly-amino acids; and albumin, gelatine, alginate, and chitosan, or derivatives thereof. Other suitable film-forming or wall-forming materials will be known to those skilled in the art.

The coat-forming fluid preferably comprises one or more agents selected from the group comprising: a pharmaceutically active agent; a taste masking agent (i.e. a sweetener); an agent that is liable to dissolution, swelling or degradation under certain defined (possibly physiological) conditions (for example a pH sensitive polymer, starch and starch derivatives, etc); a targeting compound (a ligand to a cell surface receptor overexpressed in tumour cells, i.e. vacuolar ATPases); an enhancer (short and medium chain fatty acids and their salts); a surfactant or wetting agent (tween, poloxamer, etc); and a surface stabilising agent (poloxamer, polyvinylpyrrolidone, etc).

In another embodiment, the coating may comprise a targeting moiety which is designed to target molecules, cells, tissues or organs to deliver the active agent to a desired locus. For example, the targeting moiety could be a ligand having a high affinity for a receptor that is highly expressed on the surface of tumour cells, i.e. ligands to vacuolar proton ATPases.

When spray chilling is employed, the coat-forming fluid may comprise lipids including phospholipids, waxes, surfactants such as polyethylene glycols, or low melting point polymers, all of which preferably having a melting point of 75° C. or less.

In one embodiment, the core nozzle has a diameter of between 0.7 and 2 mm. Typically, the concentric nozzle has a diameter of between 1.4 and 4 mm. Preferably, the core nozzle has a diameter of about 1 mm and the concentric nozzle has a diameter of about 2 mm. Alternatively, the core nozzle has a diameter of about 1.5 mm and the concentric nozzle has a diameter of about 3 mm. Alternatively, the core nozzle has a diameter of about 2 mm and the concentric nozzle has a diameter of about 4 mm. Generally, the diameter of the core nozzle is between 40% and 60%, preferably about 50%, the diameter of the concentric nozzle.

Suitably, the core and coat-forming fluid streams have a flow rate of up to 25 ml/min depending on the viscosity of the solution and the pump setting.

The droplets formed by the nozzle are dried as they leave the nozzle and pass through the heated gas. In a spray drying process, the gas is hot air or a heated inert gas such as nitrogen, typically having an inlet temperature of between 80° C. and 220° C. (preferably between 90° C. and 110° C., and ideally about 100°, when heated nitrogen is used). Suitably, the heated nitrogen has an outlet temperature of between 40° C. and 70° C.

When heated air is used, the inlet temperature has a range 120-220° C. and the outlet temperature between 60° C. and 160° C.

The methods described above are suitable for forming microcapsules having a core encapsulated by a single coat. In this regard, encapsulation may be complete or partial encalsulation. However, the method may be employed to produce microcapsules having two or more coats. Thus, the nozzle may comprise at least one further nozzle formed concentrically about the second nozzle and through which a further coat-forming fluid stream is sprayed. The use of multiple coats can have advantages in the sequential and controlled delivery of more than one active agent. Thus, for example, a microcapsule may be formed comprising a core containing a first active, a first coat comprising a second active, and an outer coat. In use, such a microcapsule would have a delayed release of the actives, with the second active being released first (but only after the outer coat is degraded), and the first active being delivered last. Alternatively, the components of the microcapsule could be chosen such that a sustained release of active is achieved through the provision of a number of different coats.

In one embodiment of the invention, the core consists essentially of the active agent, and the coat comprises a surfactant or surface stabilising agent such as poloxamer, wherein the microcapsules have an average diameter of less that 5µ, and preferably less than 1µ. In this embodiment, the coating prevents aggregation of the microcapsules. This is applicable to poorly soluble drugs, as a means of increasing the solubility, dissolution rate, and absorption and bioavailability of the poorly soluble active.

The invention also provides microcapsules obtainable by a method of the invention. Typically, the microcapsules have a mean diameter of less than 125µ, preferably less than 50µ, preferably less than 40µ, preferably less than 30µ, preferably less than 20µ, preferably less than 10µ, preferably less than 5µ, preferably less than 4µ, preferably less than 3µ, preferably less than 2µ, preferably less than 1.5µ. In one embodiment, the microcapsules of the invention have a mean diameter of about, or less than, 1.5µ.

The invention also relates to a microcapsule having a solid or fluid core encapsulated within at least one solid coat, and having a mean diameter of less than 125µ, preferably less than 50µ, preferably less than 40µ, preferably less than 30µ, preferably less than 20µ, preferably less than 10µ, preferably less than 5µ, preferably less than 4µ, preferably less than 3µ, preferably less than 2µ, preferably less than 1.5µ. In one embodiment, the microcapsules of the invention have a mean diameter of about, or less than, 1.5µ.

The invention also provides a preparation of microcapsules obtainable by a method of the invention. Typically, 50% of the microcapsules in the preparation have a diameter of less than 125µ, preferably less than 50µ, preferably less than 40µ, preferably less than 30µ, preferably less than 20µ, preferably less than 10µ, preferably less than 5µ, preferably less than 4µ, preferably less than 3µ, preferably less than 2µ, preferably less than 1.5µ. In one embodiment, 50% of the microcapsules in the preparation have a diameter of about, or less than, 1µ.

The invention also relates to a preparation of microcapsules, each microcapsule having a solid or fluid core encapsulated within at least one solid coat, wherein 50% of the microcapsules in the preparation have a diameter of less than 125µ, preferably less than 50µ, preferably less than 40µ, preferably less than 30µ, preferably less than 20µ, preferably less than 10µ, preferably less than 5µ, preferably less than 4µ, preferably less than 3µ, preferably less than 2µ, preferably less than 1.5µ. In one embodiment, 50% of the microcapsules in the preparation have a diameter of about, or less than, 1µ.

The method of determining the diameter of 50% of the microcapsules in a preparation ($D_{50\%}$) is described in the Examples.

Typically, the solid coat comprises a a film-forming or wall-forming material, suitably selected from the group comprising: polymer; lipid; wax; surfactants; surface stabilising agents; and ligands suitable for targeting the microcapsules to a specific desired site of action in the body. Suitably, the polymer is selected from the group comprising: methacrylate polymers such as Eudragit polymers; ethylcellulose polymers; biodegradable polyesters such as poly-lactide (PLA), poly-glycolide (PGA)_and copolymers of lactic and glycolic acid, poly-lactide-co-glycolide (PLGA, poly-caprolactone (PCA); poly-amino acids; albumin; gelatine; alginate; and chitosan. Other suitable film-forming or wall-forming materials will be known to those skilled in the art.

The solid coat preferably comprises one or more agents selected from the group comprising: a pharmaceutically active agent; a taste masking agent (i.e. a sweetener); an agent that is liable to dissolution, swelling or degradation under certain defined (possibly physiological) conditions; a targeting compound; an enhancer; a surfactant or wetting agent; and a surface stabilising agent.

In another embodiment, the coating may comprise a targeting moiety which is designed to target cells, tissues or organs to deliver the active agent. For example, the targeting moiety could be a ligand having a high affinity for a receptor that is highly expressed on the surface of tumour cells, i.e. ligands to vacuolar proton ATPases.

When fluid, the core may be a liquid or a gas. When it is of a liquid nature, it is selected from the group comprising: a solution; a suspension; a dispersion; a colloidal solution or dispersion; an oil; and an emulsion. Suitably, the core-forming liquid comprises an active compound or substance, optionally in combination with one or more pharmaceutically acceptable excipients. The active compound or substance may be any type of therapeutic, prophylactic, diagnostic, or prognostic agent. Further, it may be an agent used in imaging or labelling. In one preferred embodiment, the agent may be a pharmaceutically active agent that is required to be released in a controlled manner; thus, the coating may be designed to break down slowly in a physiological environment to release the encapsulated core over a period of time.

Typically, the core comprises a material/substance that is different to the material/substance of the coating.

Optionally the core may include a sustained release polymer with the coat being a second controlled release polymer with/without one or more targeting moieties In one embodiment, the fluid core may comprise or consist of a gas or a volatile solvent such as but not limited to ethanol, acetone, or ethylacetate. The gas may be selected from the group comprising: air; an inert gas; and a gas suitable for imaging applications. The use of a gaseous core finds particular application in microcapsules for pulmonary delivery, the gaseous core providing a microcapsule of low density more suited for delivery as an aerosol.

The invention also relates to a vehicle for delivering an active agent to the body, the vehicle comprising a microcapsule according to the invention, and wherein the active agent is located in the core or a coating of the microcapsule. Suitably, the route of administration is selected from the group comprising: oral; buccal; nasal; pulmonary; parenteral; topical; and ocular. Microcapsules according to the invention may be further formulated into a suitable pharmaceutical form such as, for example, a capsule, a tablet including fast-melt type tablets, dispersed in a suitable vehicle, incorporated into a gel, cream or lotion, ophthalmic preparation, or any other pharmaceutical form known to those skilled in the art.

The invention also relates to a vehicle for pulmonary delivery of an active agent comprising a microcapsule according to the invention and in which the core preferably comprises a gas. Typically, the core comprises at least 10%, preferably at least 20%, preferably at least 30%, preferably at least 40%, and preferably at least 50%, gas. Preferably, the core consists essentially of a gas. In one embodiment, the outer coat of the microcapsule comprises molecules suitable for targeting the microcapsule to a desired site of action in the lungs. Ideally, the microcapsule is essentially hollow (the core is essentially gaseous).

The invention also relates to a vehicle for delivering an active agent of undesirable taste to the body and comprising a microcapsule according to the invention, wherein the active agent is located in the core of the microcapsule, and wherein the at least one coating encapsulating the core masks the unpleasant taste of the active agent located in the core.

DETAILED DESCRIPTION OF THE INVENTION

The invention will be more clearly understood from the following description of some embodiments thereof, given by way of example only, in which:

FIG. 1 is an illustration of a conventional spray drying nozzle;

FIG. 2 is an illustration of a spray drying nozzle according to one embodiment of the invention;

FIG. 3 is an illustration of microcapsules formed according to the process of the invention;

FIG. 4 (samples 5 and 6) are illustrations of sodium diclofenac coated microcapsules formed according to the process of the invention;

FIG. 4 (sample 7) is an illustration of insulin coated microcapsules formed according to the process of the invention; and FIG. 4 (sample 8) is an illustration of ethylcellulose/diclofenac microparticles formed according to a conventional spray drying process.

This invention relates to a new method of producing microcapsules for application as controlled release and/or sustained release and/or targeted delivery of actives including biologicals. In one embodiment, the method includes forming a preparation of microcapsules by spray drying two streams of fluid simultaneously through a 2 concentric nozzle system. These microcapsules can include one or more therapeutic, prophylactic or diagnostic agent alone or in combination as core with a coating of one or more film forming polymer, lipids or other coating material such as targeting ligands. The core of the microcapsule may be solid or fluid depending on application. The inner core may contain the active solubilised in a suitable solvent or dispersed in a suitable vehicle or may be formulated as an emulsion.

Microencapsulation is a widely utilised process in the pharmaceutical industry for applications in delayed release, sustained release and targeting of administered drugs to their optimum site of absorption and/or action. In addition microencapsulation can be used to mask unpleasant taste and to protect drug from environmental influences such as oxidation or interaction with other incompatible material/actives. A range of techniques exist for microencapsulation including coacervation, solvent evaporation from emulsions, and fluid bed coating. Spray drying is among the most efficient and widely used technique for the drying of liquids and slurries. It is reliable, reproducible and is a one step continuous procedure offering easy scale-up. Spray drying is a technique where a liquid stream is sprayed through a nozzle into a chamber with hot circulating air. Droplets formed at the nozzle are dried in the hot air resulting in the formation of particles. The resulting dried material usually is microparticles consisting of a uniform mix of the various components of the spray dried solution as shown in comparative FIG. 1 below.

Experimental

Referring to FIG. 2, the process of the invention employs a nozzle system 1 which can allow two streams of liquid, namely a core-forming stream 2 and a coating-forming stream 2, be sprayed simultaneously from the nozzle tip 4. Microcapsules which contain a drug coated with a suitable coating material can be prepared. The drug solution can be sprayed from the inner nozzle core while the polymer or other coating solution can be sprayed from the outer nozzle core resulting in a two layered particle formed at the nozzle tip. Unlike other encapsulation technology e.g., in solvent evaporation from emulsions, where the solvents used must be immiscible, this new technology allows formation of microcapsules using liquids which are completely miscible e.g. water and ethanol, acetone and ethanol, ethylacetate and ethanol, ethanol and ethanol as the 2 feed solutions remain isolated until the point of contact at nozzle. This technology can also be used to coat liquids or drug dissolved in a liquid vehicle where the liquid is sprayed from the inner core. It can also be used to prepare hollow microspheres for pulmonary applications or for imaging where the inner liquid may be replaced by a suitable solvent/gas.

Using this double nozzle system, the polymers, Eudragit E100 or PLGA (RG504H), were spray dried as the outer coating solution with sodium Fluorescein as a model drug in the inner core solution, microcapsules containing a defined core of sodium fluorescein were prepared and examined by confocal microscopy. Formulations 1 and 3 resulted in microcapsules shown as samples 1 and 3 in FIG. 3. For samples 2 and 4, the model drug, sodium fluorescein was mixed with the Eudragit E100 polymer to increase the viscosity of the inner core solution and this was spray dried successfully with a coating solution of Eudragit E100 to give microcapsules containing the Sodium fluorescein/Eudragit E as an inner core and Eudragit E as outer coat. In sample 4, the coating solution used was at a higher concentration of 10% w/v of Eudragit E100.

Examples 2 and 4 also provide examples of formulations where the inner core, consist of an active formulated with a polymer matrix and the coat being a controlled release polymer.

The formulation and spray drying parameters used to prepare samples 1, 2, 3 and 4 are given in examples 1-4 below. The coating solution was pumped through the outer nozzle using the integral Bucchi peristaltic pump of the spray drier. The core solution was sprayed through the inner nozzle using an external peristaltic pump. The external pump used in these examples were an Ecoline VC-280, model ISM 1078 fitted with a Tygon tubing of Internal diameter 4.06 mm. This tubing was connected to a second tubing of internal diameter 2.2 mm which then connects to the feed port of the inner nozzle. The solutions were sprayed at a rate of 4-6 ml per minute, equivalent to a Bucchi integral pump setting of 16 and the external Ecoline vc-280 pump setting of 1, into the drying chamber at an inlet temperature of 100° C. The outlet temperature was monitored throughout the drying process and was similar for all 4 formulations, ranging from 48° C.-65° C.

The spray drying was carried out using a Buchi B-290 mini spray dryer fitted with an inert loop B-295 to allow the safe spray drying of inflammable solvents. The spray drier can be used in an open mode cycle where air is used for the drying of aqueous based formulations or in the closed cycle when the B-295 inert loop is switched on to provide drying in an inert atmosphere i.e., in absence of air. The closed cycle mode is used when the formulations are prepared using inflammable solvents including ethanol, acetone, dichloromethane, toluene, ethylacetate. For the example formulations 1-4, the B-290 Buchi spray drier was operated in a closed cycle using the inert solvent loop at a temperature of −20° C. to keep the system cool and condense the volatile solvents and instead of air, the solutions were spray dried in an atmosphere of nitrogen.

Spray drying techniques are well known to those skilled in the art and are described in 'Spray Drying Handbook' by K. Masters, John Wiley & Sons, New York, 1984 and in the Buchi spray drying training papers, Buchi Labortechnik AG 1997, 1998. Generally, during spray drying, besides atomizing a continuous liquid feed, a rotary atomizer can also be employed. In this invention, the two liquid feeds were continuously fed through the double nozzle and atomized using compressed nitrogen. The droplets were then dried in an atmosphere of Nitrogen. The particles of this invention are obtained by spray drying using an inlet temperature of 80 to 220° C. preferably between 80 to 160° C., depending on the solvent and an outlet temperature of between 40° C. to 120° C. The Nitrogen flow rate used was 600 L/hour and the aspirator setting used was 30 m$^3$/hour Using this double nozzle system and the process as described above, the polymers, Ethylcellulose, Eudragit E100 or chitosan were spray dried as the outer coating solution with either sodium diclofenac, simvastatin or insulin and the fluorescent marker, sodium fluorescein in the inner core solution, microcapsules containing a defined core of the drug were prepared. The diameter of the Tygon tubing used for examples 5-7 are 0.8 mm and 4 mm for the internal and external diameter respectively. The microcapsules were examined by transmission electron microscopy (TEM). Details of the formulation and spray drying parameters are given in examples 5-7 below.

Materials:

The polyester, Poly-lactide-co-glycolide polymer, Resomer RG504H with i.v of was obtained from Boehringer Ingleheim Pharma GmbH (Germany), Eudragit E 100 was obtained from Degussa, (Germany). Ethylcellulose was purchased from Sigma-Aldrich. Chitosan of medium molecular weight was purchased from sigma-Aldrich. Fluorescein sodium was obtained from Sigma. Sodium diclofenac, GMP grade, was obtained from Dipharma Francis (Milano, Italy), Bovine insulin was obtained from Sigma-Aldrich and Simvastatin, GMP grade was obtained from Leo Chem (Changzhou, China)

EXAMPLES

Example 1

A solution of Eudragit E100 was prepared by dissolving 4.95 g of Eudragit E100 polymer in 100 mls of ethylacetate using a magnetic stirrer. 50 mg of Sodium fluorescein was dissolved in 100 mls of ethanol in a separate Duran bottle to make a solution containing 0.05% w/v of sodium fluorescein and 4.95 g of Eudragit E 100. The Eudragit E100 solution was used as the coating solution and was pumped through the outer nozzle using the integral Bucchi pump at a setting of 16. The sodium fluorescein solution was used as the core solution and was pumped through the inner nozzle using the Ecoline vc-280 peristaltic pump at a setting of 1.

Using the process and equipment as described in the Experimental above, the Eudragit E100 solution and sodium fluorescein were spray dried to give microcapsules as shown in FIG. 3, Sample 1. The size of the microcapsules measured by a Malvern Mastersizer Model 2000 fitted with the Scirocco 2000(A) attachment for dry powder analysis, showed that 50% of the microcapsules ($D_{50\%}$) had a diameter of 7.78+/−0.09 microns. Confocal image of the microcapsule is shown in sample 1, FIG. 3. The outlet temperature monitored during the experiment was in the range of 51-65° C.

Example 2

A solution of Eudragit E100 was prepared by dissolving 5 g of the Eudragit E100 polymer in 100 mls of ethylacetate using a magnetic stirrer. In a separate Duran bottle, a solution of Eudragit E100 was prepared by dissolving 4.95 g of Eudragit E100 polymer in 100 mls of ethanol using a magnetic stirrer. After dissouton of the Eudragit E in ethanol, 50 mg of Sodium fluorescein was added to the solution and dissolved in a separate Duran bottle to make a solution containing 0.05% w/v of sodium fluorescein. The Eudragit E100 solution was used as the coating solution and was pumped through the outer nozzle using the integral Bucchi pump at a setting of 16. The sodium fluorescein and Eudragit E100 solution was used as the core solution and was pumped through the inner nozzle using the Ecoline vc-280 peristaltic pump at a setting of 1. Using the process and equipment as described in the Experimental above, the Eudragit E100 solution and sodium fluorescein/Eudragit E100 solution were spray dried to give microcapsules as shown in FIG. 3, sample 2. The size of the dry microcapsules measured by a Malvern Mastersizer Model 2000 fitted with the Scirocco 2000(A) attachment for dry powder analysis showed that 50% of the microcapsules ($D_{50}\%$) had a diameter of 6.94+/−0.23 microns. Confocal image of the microcapsule is shown in sample 2, FIG. 3. The outlet temperature monitored during the experiment was in the range of 51-62° C.

Example 3

A solution of poly-lactide-co-glycolide, Resomer RG504H was prepared by dissolving the 1.98 g of the polymer RG504H in 100 mls of ethylacetate using a magnetic stirrer. 20 mg of Sodium fluorescein was weighed and dissolved in 100 mls of ethanol in a separate Duran bottle to make a solution containing 0.02% w/v of sodium fluorescein. The RG504H solution was used as the coating solution and was pumped through the outer nozzle using the integral Bucchi pump at a setting of 16. The sodium fluorescein solution was used as the core solution and was pumped through the inner nozzle using the Ecoline vc-280 peristaltic pump at a setting of 1.

Using the process and equipment as described in the Experimental above, the RG504H solution and sodium fluorescein were spray dried to give microcapsules as shown in FIG. 3, sample 3. The size of the microcapsules measured by a Malvern Mastersizer 2000 fitted with the Scirocco 2000(A) attachment for dry powder analysis, showed that 50% of the microcapsules had a diameter ($D_{50\%}$) of 11.53+/−0.885 microns. The outlet temperature monitored during the experiment was in the range of 48-53° C.

Example 4

A solution of Eudragit E100 was prepared by dissolving 10 g of the Eudragit E100 polymer in 100 mls of ethylacetate using a magnetic stirrer. In a separate Duran bottle, a solution of Eudragit E100 was prepared by dissolving 4.95 g of Eudragit E100 polymer in 100 mls of ethanol using a magnetic stirrer. After dissolution of the Eudragit E in ethanol, 50 mg of Sodium fluorescein was added to the solution and dissolved in a separate Duran bottle to make a solution containing 0.05% w/v of sodium fluorescein. The Eudragit E100 solution was used as the coating solution and was pumped through the outer nozzle using the integral Bucchi pump at a setting of 16. The sodium fluorescein and Eudragit E100 solution was used as the core solution and was pumped through the inner nozzle using the Ecoline vc-280 peristaltic pump at a setting of 1.

Using the process and equipment as described in the Experimental above, the Eudragit E100 solution and sodium fluorescein/Eudragit E100 were spray dried to give microcapsules as shown in FIG. 3, sample 4. The size of the microcapsules measured by a Malvern Mastersizer 2000 fitted with the Scirocco 2000(A) attachment for dry powder analysis, showed that 50% of the microcapsules ($D_{50\%}$) had a diameter of 7.1+/−0.11 microns. The outlet temperature monitored during the experiment was in the range of 50-55° C. examples described above, the core solution was successfully encapsulated with the coating polymer solution. The microcapsule samples 1, 2, 3 and 4 had a mean diameter D50% of ~7 microns as measured by dry powder analysis using the Malvern Mastersizer model. Sample 3 showed a larger D50% value of 107. The confocal images of the samples show that the microcapsules produced were small in size and were in the size range of <5 micron in all 4 examples. This size range is particularly useful in pulmonary delivery and in targeted delivery of vaccines and biologicals.

Example 5

A solution of Ethylcellulose was prepared by dissolving 2.5 g of Ethylcellulose polymer in 100 mls of ethanol using a magnetic stirrer. In a separate Duran bottle, 2.495 g of sodium diclofenac and 2.5 mg of Sodium fluorescein was dissolved in 100 mls of ethanol. The Ethylcellulose solution was used as the coating solution and was pumped through the outer nozzle using the integral Bucchi pump at a setting of (equivalent to a feed rate of 8 ml/min). The sodium fluorescein and sodium diclofenac solution was used as the core solution and was pumped through the inner nozzle using the Ecoline vc-280 peristaltic pump with tubing diameter of 4.0 mm at a setting of 10 (equivalent to a feed rate of 4 ml/min).

Using the process and equipment as described in the Experimental section above, the ethylcellulose solution and sodium fluorescein and sodium diclofenac were spray dried to give microcapsules as shown in FIG. 4, sample 5 & 6. The size of the microcapsules as shown by the scale on FIG. 4, sample 5 were found to be less than 1 micron in diameter. The outlet temperature monitored during the experiment was in the range of 45° C.

Example 6

A solution of chitosan was prepared by dissolving a 0.5 g of chitosan polymer in 50 mls of a 1% v/v aqueous solution of acetic acid. In a separate Duran flask, 20 mg of from bovine insulin and 10 mg of sodium fluorescein were dissolved in 50 mls of a 1% v/v aqueous solution of acetic acid. The chitosan solution was used as the coating solution and was pumped through the outer nozzle using the integral Bucchi pump at a setting of 14 (equivalent to a feed rate of 4 ml/min). The insulin solution was used as the core solution and was pumped through the inner nozzle using the Ecoline vc-280 peristaltic pump with tubing diameter of 4.0 mm at a setting of 10 (equivalent to a feed rate of 4 ml/min).

Using the process and equipment as described in the Experimental section above, the chitosan polymer solution and the sodium fluorescein solution and insulin solution were spray dried at an inlet temperature of 170° C. to give microcapsules as shown in FIG. 4, sample 7.

The size of the microcapsules measured by a Malvern Mastersizer Model 2000 using a wet dispersion analysis method, showed that 50% of the microcapsules ($D_{50\%}$) had a diameter of 12.14+/−1.17 microns.

The outlet temperature monitored during the experiment was in the range of 87-90° C.

Example 7

A solution of simvastatin was prepared by dissolving 0.625 g of simvastatin in 25 mls of ethanol using a magnetic stirrer. In a separate Duran bottle, 1.875 g of Eudragit E100 polymer was dissolved in 25 mls of ethanol to make a solution containing 2.5% and 7.5% w/v of total drug and polymer respectively. The Eudragit E100 solution was used as the coating solution and was pumped through the outer nozzle using the integral Bucchi pump at a setting of 15. The simvastatin solution was used as the core solution and was pumped through the inner nozzle using the Ecoline vc-280 peristaltic pump at a setting of 10.

Using the process and equipment as described in the Experimental section above, the ethylcellulose solution and sodium fluorescein and sodium diclofenac were spray dried at an inlet temperature of 55° C. to give microcapsules. The size of the microcapsules measured by a Malvern Mastersizer Model 2000 fitted with the Scirocco 2000(A) attachment for dry powder analysis, showed that 50% of the microcapsules ($D_{50\%}$) had a diameter of 8.40+/−0.08 microns. The outlet temperature monitored during the experiment was in the range of 33-37° C.

In the examples 1-7 described above, the Buchi Three Fluid Nozzle was employed, having a core nozzle diameter of 1 mm and a concentric nozzle diameter of 2 mm.

Example 8

For comparison, a solution of Ethylcellulose and sodium diclofenac was prepared by dissolving 7.5 g of Ethylcellulose polymer and 2.5 g of sodium diclofenac in 100 mls of ethanol using a magnetic stirrer. The Ethylcellulose and sodium diclofenac solution was spray dried using the Buchi lab spraydrier fitted with the conventional nozzle with diameter 0.7 mm. The solution was pumped using the integral Bucchi pump at a setting of 36 and aspirator setting of 86. The inlet temperature used was 100° C.

The microcapsules were examined by TEM and are shown in FIG. 4, sample 8. The size of the microcapsules as shown by the scale on FIG. 4 were found to be less than 1 micron in diameter. The outlet temperature monitored during the experiment was recorded to be 60° C.

The invention provides microcapsules for delivering active agents in a controlled and/or targeted manner. The active agents may be healthcare, cosmetic or food related. When the active agents are healthcare related (i.e. therapeutic agents) methods of introduction include but are not limited to intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the microcapsules of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the microcapsules of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

The present invention also provides pharmaceutical compositions comprising microcapsules of the invention. Such compositions comprise a therapeutically effective amount of a therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention is not limited to the embodiments herein before described which may be varied in both construction and detail without departing from the spirit of the invention.

The invention claimed is:

1. A method of producing microcapsules by spray-drying, the microcapsules having a D50% of less than 125 µm, and a core and a coating encapsulating the core, the method comprising the steps of providing a core-forming fluid stream and a coating-forming liquid stream, providing a two spray nozzle arrangement having a tip with an outer nozzle disposed concentrically about a core nozzle, spraying the core-forming fluid stream from the core nozzle and the coating-forming liquid stream from the outer nozzle to produce atomised droplets, and drying the droplets in a heated gas to produce the microcapsules.

2. A method as claimed in claim 1 in which the core-forming fluid is a liquid, a volatile solvent or a gas.

3. A method as claimed in claim 2 in which the core-forming liquid comprises an active compound or substance, optionally in combination with at least one pharmaceutically acceptable excipient.

4. A method as claimed in claim 1 in which the coating-forming liquid stream comprises a coating material selected from the group comprising: polymer; lipid; wax; surfactants; surface stabilising agents; and ligands suitable for targeting the microcapsules to a specific desired site of action in the body.

5. A method as claimed in claim 4 in which the polymer is a film-forming polymer or a wall-forming polymer.

6. A method as claimed in claim 1 in which the nozzle comprises at least one further nozzle formed concentrically about the outer nozzle and through which a further coat-forming liquid stream is sprayed.

* * * * *